United States Patent [19]

Olstein et al.

[11] Patent Number: 5,750,357
[45] Date of Patent: May 12, 1998

[54] METHOD OF RAPID ANALYTE DETECTION

[75] Inventors: Alan D. Olstein, Mendota Heights; Richard Albert, Eden Prairie, both of Minn.

[73] Assignee: MicroQuest Diagnostics, Inc., Eden Prairie, Minn.

[21] Appl. No.: 380,643

[22] Filed: Jan. 30, 1995

Related U.S. Application Data

[63] Continuation-in-part of Ser. No. 245,374, May 18, 1994, abandoned.

[51] Int. Cl.⁶ ........................ G01N 33/569; G01N 33/53
[52] U.S. Cl. ........................ 435/7.32; 435/7.1; 435/7.2; 435/7.9; 436/501; 436/518; 436/534
[58] Field of Search ........................ 435/7.1, 7.9, 7.32, 435/7.2; 436/501, 518, 534

[56] References Cited

U.S. PATENT DOCUMENTS

| | | | |
|---|---|---|---|
| 4,166,105 | 8/1979 | Hirshfeld et al. | 424/8 |
| 4,169,137 | 9/1979 | Hirshfeld et al. | 424/8 |
| 4,242,447 | 12/1980 | Findl et al. | 435/39 |
| 4,525,453 | 6/1985 | Guardino et al. | 435/34 |
| 4,687,732 | 8/1987 | Ward et al. | 435/6 |
| 4,868,110 | 9/1989 | DesRosier et al. | 435/34 |
| 5,137,812 | 8/1992 | Matner | 435/36 |
| 5,168,063 | 12/1992 | Doyle et al. | 435/240 |
| 5,169,599 | 12/1992 | Joseph et al. | 422/57 |
| 5,369,036 | 11/1994 | Mercolino et al. | 436/523 |
| 5,403,720 | 4/1995 | Sato et al. | 435/31 |
| 5,403,721 | 4/1995 | Ward, Jr. et al. | 435/34 |
| 5,415,997 | 5/1995 | Atrache et al. | 435/7.35 |
| 5,416,002 | 5/1995 | Steele et al. | 435/8 |
| 5,420,017 | 5/1995 | Tuompo et al. | 435/29 |
| 5,543,332 | 8/1996 | Lihme et al. | 436/528 |

FOREIGN PATENT DOCUMENTS

| | | |
|---|---|---|
| 0 077 671 | 4/1983 | European Pat. Off. |
| WO 84/04970 | 12/1984 | European Pat. Off. |
| 0 265 127 | 4/1988 | European Pat. Off. |
| 0 277 697 | 8/1988 | European Pat. Off. |
| WO 91/12282 | 8/1991 | European Pat. Off. |
| 0 460 385 | 12/1991 | European Pat. Off. |
| 2295426 | 7/1976 | France . |
| 2025372 | 1/1980 | United Kingdom . |
| WO 92/22669 | 12/1992 | WIPO . |

OTHER PUBLICATIONS

B.J. Appelmelk et al., "Polymyxin B–Horseradish Peroxidase Conjugates as Tools in Endotoxin Research", *Analytical Biochemistry*, 207, pp. 311–316, (1992).

B.W. Blais et al., "Application of Polymyxin–Coated Polyester Cloth to the Semi–Quantitation of Salmonella in Processed Foods", *International Journal of Food Microbiology*, 14, pp. 43–50, (1991).

B.W. Blais et al., "Use of Polymyxin–Coated Polyester Cloth in the Enzyme Immunoassay of Salmonella Lipopolysaccharide Antigens", *International Journal of Food Microbiology*, 11, pp. 195–204, (1990).

S. Chihara et al., "Enzymatic Degradation of Colistin Isolation and Identification of α–N–Acyl αγ–Diaminobutyric Acid and Colistin Nonapeptide", *Agr. Biol. Chem.*, 37, pp. 2455–2463, (1973).

R.L. Danner et al., "Purification, Toxicity, and Antiendotoxin Activity of Polymyxin B Nonapeptide", *Antimicrobial Agents and Chemotherapy*, 33, pp. 1428–1434, (Sep. 1989).

P.M. Fratamico et al., "Rapid Isolation of *Escherichia Coli* 0157:H7 From Enrichment Cultures of Foods Using an Immunomagnetic Separation Method", *Food Microbiology*, 9, pp. 105–113, (1992).

H.E. Gilleland, Jr., "Adaptive Alterations in the Outer Membrane of Gram–Negative Bacteria During Human Infection", *Can. J. Microbiol.*, 34, pp. 499–501, (1988).

A.C. Issekutz, "Removal of Gram–Negative Endotoxin From Solutions by Affinity Chromatography", *Journal of Immunological Methods*, 61, pp. 275–281, (1983).

G. Kobayashi, "Fungi", In: *Microbiology*, Chapter 43, B. Davis, et al. (eds.) Harper & Row, Hagerstown, Maryland, pp. 983–984 (1973).

P. Kubesch et al., "Interaction of Polymyxin B Nonapeptide with Anionic Phospholipids", *Biochemistry*, 26, pp. 2139–2149, (1987).

M.S. Kim et al., "Dipstick Immunoassay to Detect Enterohemorrhagic Escherichia Coli 0157:H7 in Retail Ground Beef", *Applied and Environmental Microbiology*, 58, pp. 1764–1767, (May 1992).

R.A. Moore et al., "Interaction of Polycationic Antibiotics with Pseudomonas aeruginosa Lipopolysaccharide and Lipid A Studied by Using Dansyl–Polymyxin", *Antimicrobial Agents and Chemotherapy*, 29, pp. 496–500, (Mar. 1986).

H. Nikaido et al., "Molecular Basis of Bacterial Outer Membrane Permeability", *Microbiological Reviews*, 49, pp. 1–32, (Mar. 1985).

C. R. H. Raetz, "Biochemistry of Endotoxins", *Annu. Rev. Biochem.*, 59, pp. 129–170, (1990).

P.E. Reynolds, "Structure, Biochemistry and Mechanism of Action of Glycopeptide Antibiotics", *Eur. J. Clin. Microbiol. Infect. Dis.*, 8, pp. 943–950, (Nov. 1989).

M. Schindler et al., "Interaction of Divalent Cations and Polymyxin B with Lipopolysaccharide", *Biochemistry*, pp. 4425–4430, (1979).

(List continued on next page.)

*Primary Examiner*—Toni R. Scheiner
*Attorney, Agent, or Firm*—Mueting, Raasch & Gebhardt, P.A.

[57] ABSTRACT

A detectable synthetic copolymer useful to detect the presence of a microorganism in a test sample is provided. The copolymer comprises repeating monomeric units, which incorporate a population of first monomeric units each comprising a binding agent which binds to a microorganism having multiple binding sites for said binding agent and which further incorporates a population of a second monomeric units each comprising a detectable label or a binding site for a detectable label.

32 Claims, No Drawings

OTHER PUBLICATIONS

P. R. G. Schindler et al., "Action of Polymyxin B on Bacterial Membranes: Morphological Changes in the Cytoplasm and in the Outer Membrane of *Salmonella typhimurium* and *Escherichia coli* B", *Antimicrobial Agents and Chemotherapy*, 8, pp. 95–104, (Jul. 1975).

R. Szabo et al., "Increased Sensitivity of the Rapid Hydrophobic Grid Membrane Filter Enzyme–Labeled Antibody Procedure for *Escherichia coli* 0157 Detection in Foods and Bovine Feces", *Applied and Enviromental Microbiology*, 56, pp. 3546–3549, (Nov. 1990).

M. Vaara et al., "Polycations Sensitize Enteric Bacteria to Antibiotics", *Antimicrobial Agents and Chemotherapy*, 24, pp. 107–113, (Jul. 1983).

M. Vaara et al., "Sensitization of Gram–Negative Bacteria to Antibiotics and Complement by a Nontoxic Oligopeptide", *Nature*, 303, pp. 526–528, (Jun. 1983).

A. Vertut–Croquin et al., "Differences in the Interaction of the Polyene Antibiotic Amphotericin B with Cholesterol–or Ergosterol–Containing Phospholipid Vesicles, A Circular Dichroism and Permeability Study" *Biochemistry*, 22, pp. 2939–2944, (1983).

METHOD OF RAPID ANALYTE DETECTION

CROSS-REFERENCE TO RELATED APPLICATION

This application is a continuation-in-part of U.S. patent application Ser. No. 08/245,374 filed May 18, 1994, now abandoned.

FIELD OF THE INVENTION

The present invention relates to a method for rapidly detecting analytes including pathogenic agents such as coliform bacteria and fungi.

BACKGROUND OF THE INVENTION

The term "coliform bacteria" as used herein refers to a group of bacterial genera made up of Escherichia, Klebsiella, Enterobacter, Serratia and Citrobacter bacteria. Coliform bacteria tend to be small, gram negative rods that may be either motile or nonmotile. Coliform bacteria have complex membranes that include murein, lipoprotein, phospholipid and lipopolysaccharide (LPS) components arranged in layers. A murein-LPS layer is about 20% of the total bacterial membrane and is responsible for bacterial cell rigidity. The LPS aids in preventing hydrophobic toxins from entering a coliform bacterial cell. The LPS is capable of releasing an endotoxin into a host once coliform bacteria infect the host. In human hosts, the endotoxin is released into the bloodstream.

Natural competitors of coliform bacteria have evolved secondary metabolites, such as antibiotics, to overcome the LPS defense. Competitors such as soil fungi and Streptomycetes as well as gram positive bacteria produce antibiotics. One particular class of lipopeptide antibiotic, polymyxins, are produced by a soil microorganism, *B. polymyxa*.

The polymyxins are designated by the letters A, B, C, D and E. The polymyxins are toxic to coliform bacteria because these antibiotics bind to the LPS in an outer membrane of the coliform bacteria and disrupt cellular metabolism of a coliform bacterium once translocated to an inner cytoplasmic membrane. In particular, the polymyxins are believed to alter the structure and osmotic properties of the outer membrane. Intact, polymyxin antibiotics are capable of binding to both animal membranes and coliform bacterial membranes.

Coliform bacteria as well as some fungi may cause infections in the urinary tract and wounds of a human host. Coliform bacteria may also cause pneumonia, meningitis, septicemia and various gastrointestinal disorders in a human being. It has been estimated that as many as 100,000 deaths in the United States each year are a consequence of gram negative bacteria infections such as coliform bacteria.

In addition to causing disease by direct infection, the endotoxin produced by coliform bacteria produces a variety of effects, such as fever, fatal shock, leukocytic alterations, cytotoxicity, alterations in host response to infections, Sanarelli-Shwartzman reaction and various other undesirable metabolic changes. When coliform bacteria enter the bloodstream of a human being, endotoxic shock plays an important role in weakening the individual. About 30% of individuals with endotoxin in their blood will develop shock. About 40 to 90% of individuals in endotoxic shock die. Endotoxin shock is characterized by an inadequacy of blood supply to vital organs of the host causing cellular hypoxia and metabolic failure. Survival of the host is directly proportional to the length of time needed to recognize the development of bacteremia and adequate treatment of the coliform bacterial infection.

Unfortunately, to date, testing for coliform bacteria, yeast and fungi has been excessively time consuming and labor intensive. While the onset of symptoms from the endotoxin may be exceedingly rapid, laboratory based diagnosis will typically take days. To detect and identify coliform bacteria, it is necessary to expose suspect specimens, such as sputum, tissue, pus, body fluids, rectal swabs or feces to a culture media that will allow the growth of gram negative bacteria but inhibit the growth of gram positive bacteria.

The present techniques used for this type of screening involve aseptic transfer of a sample, streaking the sample having bacterial organisms on agar plates after serial dilution and colony enumeration. This is a laborious and lengthy process requiring a time of at least about 24 to 48 hours for a positive result and substantially longer for a negative result.

Additionally, test solutions containing enteric bacteria, use carbohydrates and acid based indicators to demonstrate carbohydrate fermentation. Lactose and analogues of lactose are the carbohydrates most frequently used in bacteria testing. This is because the majority of organisms of the genera Escherichia, Enterobacter, and Klebsiella, the enteric organisms present in greatest number in fecal material, ferment this carbohydrate while other intestinal pathogens usually do not. Some media may also contain iron salts for the detection of hydrogen sulfide production to aid in the identification of Salmonella colonies. This approach to bacterial testing also requires a lengthy incubation time to grow enough bacteria for testing, at least 24 to 48 hours.

Other analyte tests require an organism to digest a detectable material such as fluorescein. In other tests, an antibody, specific for an antigen on an analyte, is labeled with fluorescein to make a fluorescent antibody.

The Ward et al. patent, U.S. Pat. No. 4,687,732, generally describes a detection-visualization composition made up of a visualization polymer. This polymer is in turn made up of detectable visualization units, such as multiple enzymes or labelled polyolefins, which are directly or indirectly bonded together. The visualization polymer is coupled to a detecting agent for the target analyte molecule, such as an antibody, an enzyme, or a strand of DNA receptor protein.

However, a continuing need exists for a sensitive and rapid method to detect extremely small amounts of target biological analytes.

SUMMARY OF THE INVENTION

The present invention provides a detectable synthetic polymer comprising repeating monomeric units, wherein a first population of monomeric units each comprises a binding agent, such as an antibiotic, which binds to a microorganism, such as a pathogenic bacterium, having multiple binding sites for said binding agent and wherein a second population of monomeric units each comprises a detectable label, such as a fluorogenic molecule, or a binding site for a detectable label, such as biotin. Preferably, the polymer includes more of said second monomeric units than of said first monomeric units, i.e., at least a ten-fold excess of the second monomeric units over the first monomeric units.

The present detectable synthetic polymer is employed in an assay method to detect the presence in a sample, such as a liquid sample, of microorganisms, such as bacteria. In the practice of the method, the microorganisms are first immobilized, as on a filter, and contacted with an excess amount of the detectable synthetic polymer. The binding agent, i.e., the antibiotic or a fragment thereof, is preselected to bind to a target population of microorganisms, such as gram positive or gram negative bacteria. Since, preferably, there are multiple binding sites for the binding agent on each target organism, and the number of detectable labels, or binding sites therefore, exceeds the number of binding agents on the detectable polymer, so that the resultant signal is greatly amplified relative to the number of organisms which are initially bound. In some cases, the efficient binding of the binding agents to multiple sites on each organism will enable a detectable complex of, e.g., an antibiotic and a detectable label or a binding site for a detectable label to be visualized with sufficient sensitivity. In other cases, the organisms can be first reacted with an antibiotic coupled to a binding site for a detectable label, and the binding site is subsequently reacted with a labelled compound, such as a polymer comprising a multiplicity of detectable labels, as will be further discussed below.

The present invention provides a method for rapidly detecting an analyte which employs a detectable linear synthetic polymer, or "chemical tag." The chemical tag includes a backbone of one of a synthetic water soluble polymer, a synthetic water insoluble polymer, and analogues and derivatives of these polymers. The chemical tag also includes a plurality of detectable components attached to the polymer backbone via linking moieties. The chemical tag additionally includes one or more binding agents, which are fewer in number than the number of detectable components. The binding agent is capable of binding with the analyte to be detected. Once bound, the analyte is detected by means of the detectable component.

The present invention also provides a detectable synthetic polymer, or "chemical tag." The chemical tag includes a backbone formed of a synthetic polymer selected from a group that includes synthetic water soluble polymers, synthetic water insoluble polymers, and analogues and derivatives of these polymers. The chemical tag also includes a plurality of detectable components, each attached to the synthetic polymer backbone via a linking moiety, as well as one or more detectable components linked to the synthetic polymer.

The method of the present invention preferably relies upon formation of a bond between an antibiotic such as polymyxin B and a lipopolysaccharide (LPS) component of the coliform bacterium such as the endotoxin produced by the bacterium. See, C. R. Raetz, *Ann. Rev. Biochem.*, 59, 129–170 (1990). This bond binds the bacterium or the endotoxin to the chemical tag. Once the bond is formed, the chemical tag can be detected via a detectable label which provides a signal that is amplified relative to the number of units of analyte due to the presence of multiple detectable sites on each tag molecule. For example, the bound tag may be detected via emissions from multiple fluorescent molecules. The chemical tag can also be detected by the incorporation thereto of molecules such as biotin, which provide binding sites for a detectable label, such as an avidin-enzyme complex. These molecules can be attached via linking moieties to monomeric units of the water soluble polymer or water insoluble polymer backbone of the chemical tag.

The method for detecting coliform bacteria and endotoxin produced by the coliform bacteria using the chemical tag of the present invention is a surprisingly rapid and sensitive assay. It is believed that the sensitivity of the chemical tag is such to decrease detectable levels of many analytes by several orders of magnitude over what is now obtainable. However, biochemical and immunochemical methods, presently available detect coliform bacteria down to about 10,000 to 100,000 organisms, the method of the present invention is capable of detecting organisms in a range of 1 to 1000 organisms. While plating methods take at least 24 hours to produce a positive result, and much longer to produce a conclusive negative result, the method of the present invention produces a conclusive result within an hour of preparing a sample of a test sample as varied as meat, blood and water.

DETAILED DESCRIPTION OF THE PREFERRED EMBODIMENTS

The present invention provides a chemical tag and method for rapid detection of a pathogenic microorganisms, e.g., a bacterium such as a coliform bacterium, a subunit thereof, or endotoxin produced by the coliform bacterium. As used herein, the term "microorganism" includes subunits thereof, such as membrane fragments and metabolites thereof, such as endotoxins. This method includes providing a biocide which binds to the bacterium, such as an antibiotic, e.g., polymyxin B, as the binding agent. A polymer comprising multiple detectable components is then bound to the antibiotic, i.e., to the polymyxin B component to make a chemical tag that produces a detectable signal once the polymyxin B component binds to the bacterium or to its endotoxin. The chemical tag is then contacted with the coliform bacterium so that the antibiotic binds to the bacterium to form a complex, and the complex is detected via the signal provided by the detectable component.

Synthetic Polymer Backbone

The chemical tag includes a polymer backbone selected from a group of water soluble polymers that includes an acrylate, a methacrylate, and polyvinyl polymers obtained from vinyl monomers such as polyvinyl alcohol, and polyvinylpyrrolidinone as well analogues and derivatives of these polymers. The chemical tag backbone may also be selected from a group of water insoluble polymers such as polystyrene as well as analogues and derivatives of polystyrene, such as alkylated polystyrenes.

Biotin and Biotin-Avidin Complexes

The chemical tag of the present invention can incorporate multiple biotin molecules covalently bonded to a population of monomers of the synthetic polymer, via linking moieties, in order to generate a powerful signal. It has been found that derivatives of biotin such as iminobiotin and desthiobiotin are also suitable for use in the chemical tag as binding sites for detectable labels. In one particular embodiment, the covalently bonded biotin molecule provides a reaction site for an avidin component of an avidin-horseradish peroxidase conjugate. In other acceptable embodiments, the biotin molecule may react with another avidin—enzyme conjugate such as an avidin—alkaline phosphatase and an avidin—beta galactosidase conjugate. Because of the strong bonds between biotin and the synthetic monomer and biotin and avidin, the chemical tag of the present invention does not have to covalently bond with the peroxidase or other enzyme. Consequently, enzyme activity is not lost by direct covalent crosslinking chemistry between enzyme molecules and a final detectable signal is maximized at each biotin site.

Polymyxin B and Subunits Thereof

Polymyxin B, like the other polymyxins, is a decapeptide having a high percentage of 2,4-diaminobutyric acid (Dab), a fatty acid and a mixture of D- and L-amino acids. Polymyxin B has the following structure:

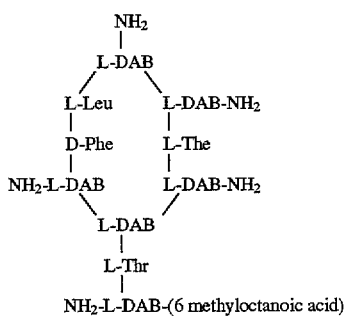

NH$_2$-L-DAB-(6 methyloctanoic acid)

In addition to the complete polymyxin B molecule, it has surprisingly been found that the peptide constituent of the polymyxin B which is formed by removal of the 6-methyloctanoic acid moiety, is also usable in the chemical tag of the present invention as the binding component. The polymyxin B molecule is digestible to form the peptide constituent and a lipid constituent that includes octanoic acid. Digestion may be accomplished with a standard proteolytic enzyme. The cyclic nonapeptide constituent may then be easily separated from the lipid constituent and purified by a method such as liquid/liquid extraction. See M. Vaara et al., *Nature*, 303, 526 (1983) and M. Vaara et al., *Antimicrobial Agents & Chemother.*, 24, 107 (1983).

The peptide constituent is a preferred constituent for use in the method of the present invention because the peptide constituent is not toxic to either animal cells or bacteria. The nontoxicity occurs because this constituent cannot bind to a cytoplasmic membrane. However, the peptide constituent does show high avidity and selectivity in binding with the LPS in the outer membrane of gram negative bacteria. This embodiment has been found to be particularly suitable for rapid coliform detection in samples contaminated with eucaryotic cell membranes such as samples of meat, poultry and dairy products. The chemical complex that includes the peptide fragment of polymyxin B is also preferred for detection of endotoxin. A chemical tag made with the peptide constituent includes coupling to a terminal amino group of the peptide fragment to one of biotin or, alternatively, directly to the synthetic polymer.

Other Antibiotic Binding Agents

Additionally, antibiotics selective for gram positive microbes are believed to be suitable binding agents for use in the present invention, such as reistocitin and vancomycin. These antibiotics are glycopeptides that act specifically to block synthesis of peptidoglycan precursors of murein building blocks in the cell walls of gram positive bacteria. Such antibiotics could be used in a manner complementary to the polymyxins to identify each of gram negative and gram positive bacteria. The chemical structure of the antibiotics lends the antibiotics either to direct coupling to the chemical tag of the present invention through a single free primary amine group on a peptide moiety, or indirect coupling through a preparation of an avidin conjugate of the antibiotic through the same amino group. A concurrent use of complexes selected for each of gram positive bacteria and gram negative bacteria could be applicable to field situations in which a knowledge of relative quantities of gram positive and gram negative bacteria are required.

One other group of antibiotics which, it is believed, could serve as binding agents include the aminoglycoside antibiotics. Specific amino glycoside antibiotics include tobramycin, kanamycin and gentamicin. The aminoglycosides are far less hydrophobic than the polymyxins and are thought to bind the LPS in an outer membrane envelope of gram negative microorganisms. The aminoglycoside antibiotics would then function in a similar fashion to the polymyxins.

One additional group of binding agents suitable for detecting eucaryotic microbes such as fungi include the polyene antibiotics such as amphotericin B and nystatin. Each of these antibiotics has a chemical functionality which lends itself to incorporation as a binding agent into the chemical complex of the present invention. This list is presented as exemplary but not exhaustive of suitable binding agents.

Antibiotic-Biotin Complexes

In an embodiment of the chemical tag, the antibiotic, i.e., the polymyxin B or the above-mentioned peptide subunit thereof, is linked to biotin to form a chemical complex which can in turn be detected with labeled avidin and/or a polymeric tag which can bind to a biotin-avidin complex.

As described, polymyxin B is active as an antibiotic against coliform bacteria. The antibiotic properties of polymyxin B are related to the molecule's capacity to bind the outer bacterial membrane at the LPS component. About one million binding sites for polymyxin B are available on each coliform bacterium. Thus, polymyxin B and the peptide constituent of polymyxin B have a very high probability of binding to some extent with each coliform bacterium present in a sample. The present invention takes advantage of this binding capacity to make a chemical tag that may be used to rapidly identify coliform bacteria in extremely small numbers within a particular sample.

In this embodiment of the present invention, the biotin molecule is attached to the polymyxin B at one of the amine sites of the polymyxin B molecule. The biotin molecule may also be attached to the amine site of the de-octanoated peptide constituent of PMB. It has surprisingly been found that this attachment does not cripple the capacity of the polymyxin B to bind to the coliform bacterium. The result is surprising because the amine groups of polymyxin B and the peptide constituent of polymyxin B directly participate in stabilization of the LPS component and outer membrane envelope of the bacterium once the polymyxin B binds to the outer membrane of the bacterium.

If biotin is employed as the binding site for a detectable label, once the polymyxin B component or peptide constituent of this complex attaches to a bacterium, the biotin on the chemical tag is detectable by reaction with labelled avidin, i.e., with avidin-horseradish peroxidase or other avidin-enzyme conjugates such as an avidin—phosphatase or avidin—beta galactosidase. The avidin component of the avidin-horseradish peroxidase binds to the biotin molecule to make a soluble colorless indicator. The colorless avidin indicator may be rapidly visualized with any of a number of colorimetric reagents that react with the horseradish-peroxidase component of the avidin-horseradish peroxidase. These reagents include diaminobenizidine, aminethylcarbazole and chloronaphthol. These colorimetric reactions require a presence of hydrogen peroxide or organic peroxides as an oxidant. When avidin is bound to a phosphatase, the indicator may be visualized with a naphthol dye. A chemical tag employing this detection system has been found to detect as few as 1000 organisms.

Polymeric Chemical Tag Comprising Antibiotic and Excess Detectable Component

In another embodiment, the chemical tag includes binding molecules that are attached to a synthetic water-soluble polymer backbone. Preferably, the chemical tag includes at least one or two polymyxin B components per synthetic polymer in order to optimize binding capacity of the complex of the chemical tag and polymyxin B to the target analyte. Preferred synthetic water-soluble polymers include acrylamide and acrylate polymers.

The synthetic water-soluble polymer backbone is attached to the polymyxin B molecule, preferably with an intermediate linking moiety that is bonded to each of the polymer and the polymyxin B. One preferred intermediate monomer includes an N-hydroxysuccinimide linking moiety, attached to a methacrylic acid monomer. This intermediate monomer is made by preparing an active ester of methacrylic acid. The active ester is prepared by reacting the methacrylic acid with a water soluble carbodiimide which is captured as the N-hydroxysuccinimide derivative forming the activated ester. The activated ester undergoes aminolysis by a sufficiently nucleophilic amine group on an incoming peptide such as polymyxin B which forms a stable amide linkage with the methacrylic ester. In one other embodiment, polymyxin B is reacted directly with an ethylaminodiethylaminopropyl carbodiimide (EDC) activated methacrylic acid. The activated carboxyl groups of the intermediate synthetic monomer bind with the polymyxin B.

In this embodiment, the water-soluble polymer backbone of the chemical tag preferably includes more than one biotin molecule. This type of chemical tag will have an amplified signal as compared to the chemical tag having polymyxin B attached to a single biotin molecule because of a presence of multiple biotin molecules, each of which can react with avidin-horseradish peroxidase and produce a measurable signal. This chemical tag embodiment has been found to detect as few as 10 organisms.

One particular chemical tag embodiment preferably additionally includes linking moieties attached to the water soluble polymer backbone. Suitable monomers include electrically neutral water-soluble moieties which are derived from acrylamide and methacrylamide. Each of the linking moieties is bound to each of the water-soluble polymer backbone and a biotin molecule.

The complex of the present invention includes another embodiment in which either of the polymyxin B polymer or peptide constituent of polymyxin B is attached to a tag compound having a synthetic water-soluble polymer backbone made up of polymerizable fluorescent monomers and an intermediate amine functional monomer. Preferred fluorescent monomers include N-fluoresceinylacrylamide and sulfonamide obtained from reaction of Sulforhodamine 101 acid chloride (Texas Red™). The fluorescent monomers are incorporated into the polymer chain at a minimum stoichiometric ratio of ten monomers to one molecule of the polymyxin B or peptide constituent.

The fluorescent monomers may be attached to the polymer backbone via reaction with neutral water soluble monomers such as acrylamide and methacrylamide that bind with each of the fluorescent molecules. A preferred intermediate amine functional monomer is N-aminopropylmethacrylamide. With this fluorescent chemical tag, a significant amplification of fluorescence can be obtained above that obtainable using previous methods. It has been found that this type of chemical tag compound can detect as few as a single organism in a test sample.

The present invention also includes a chemical tag compound having a water insoluble polymer component that is attached to the polymyxin B molecule. One preferred water insoluble polymer includes a fluorescent polystyrene microsphere of extremely small particle size, such as approximately 0.02 microns in diameter, which is attachable to the polymyxin B molecule. In one particular embodiment, a fluorescent microsphere with an aldehyde surface functionality, such as Fluosphere™, manufactured by Molecular Probes, Inc., of Eugene, Oreg. is employed.

Either of the polymyxin B molecule or the PMB peptide constituent may be attached to the fluorescent microsphere by reductive alkylation to make a chemical tag. This chemical tag avidly binds to coliform bacteria such as *E. coli* and *S. typhimurium*.

Antibiotic-Biotin-Avidin Complex

One other preferred chemical complex embodiment includes a polymyxin B polymer attached to a biotin molecule. An avidin molecule is in turn attached to the biotin molecule. After reaction of this complex with the target microorganism, a biotinylated synthetic polymer such as a biotinylated acrylamide polymer is then attached to the avidin molecule via a biotin site. This chemical tag has been found to detect and visualize a single microbe. This chemical complex is further described in Example 9.

One other preferred chemical complex embodiment includes a first water soluble polymer such as has been described, attached to the polymyxin B and a second biotinylacrylamide polymer in contact with the first polymer. This chemical complex is further described in Example 7.

The use of biotin to make a polymyxin B-biotin conjugate and by attaching multiple biotin molecules to a water soluble synthetic polymer backbone through linking moieties derived from synthetic monomers is useful directly and indirectly, respectively, not only for detecting coliform bacteria but in distinguishing bacteria utilizing lactose from non-lactose utilizing bacteria. In addition to the colorimetric reaction detecting coliform bacteria directly, the peroxidase enzyme component of the avidin-horseradish peroxidase reacts with any hydrogen peroxide that may be generated by the coliform bacterium. Detecting hydrogen peroxide by self-development permits this embodiment of the rapid coliform bacterial detection method to additionally differentiate organisms of the *Escherichia coli* genus species from other non-lactose fermenting gram negative organisms.

Frequently, in water quality monitoring, it is necessary to know not only whether water is contaminated with coliform bacteria but whether the coliform bacteria can utilize lactose. The presence of organisms utilizing lactose implicates the presence of *Escherichia coli* which is a major bacterial organism present in the lower bowel of many mammals.

Existing methods of detecting *E. coli* are cumbersome and excessively time consuming. The methods employ an enrichment culture technique in which a fluorogenic substrate is incubated with an enriched sample after a 24 hour incubation period. In accord with the rapid method of the present invention, bacteria in a test sample are briefly incubated with an inducer of β-galactosidase, such as isopropylthiogalactoside, which rapidly increases synthesis of β-galactosidase over bacterial basal levels. In the presence of added lactose, glucose and galactose are formed. The bacteria are then treated with either the polymyxin B—biotin tag or the polymyxin B—synthetic water-soluble polymer tag and are immobilized on a microporous filter.

The filter is then treated with a solution of glucose oxidase to convert glucose formed from the bacterial metabolic hydrolysis of the added lactose into gluconic acid and hydrogen peroxide. The hydrogen peroxide reacts in the presence of horseradish peroxidase (HRP) bound to avidin which, in turn, is immobilized on bacterial membranes of bacteria retained on the filter, causing a color reaction. In this manner, the chemical tag and complex of the present invention identify not only coliform bacteria generally but *Escherichia coli* in particular on the membrane filter because of *Escherichia coli*'s ability to metabolize lactose in situ.

In another embodiment, the bacteria immobilized on the filter are induced with the β-gal inducer and the tag is added.

The tagged bacteria are then treated with one of bromo or chloro indoyl or bromo- or chloro-naphthol galactoside which is hydrolyzed to galactose and bromo- or chloroindole or naphthol, which are substrates for HRP. An insoluble colored product is formed from the hydrolyzed product by a horseradish peroxidase catalyzed oxidation of the hydrolyzed product.

The methods of the present invention are suitable for use in rapidly detecting coliform bacteria in samples as diverse as drinking water, hamburger and blood. For samples of large volume and mass such as drinking water samples, the present invention includes a kit comprising, packaged together, a filter membrane as well as the chemical tag or complex described. In one embodiment, the filter membrane is a commercial 0.2 micron filter made of a sufficiently transparent material to permit direct insertion of the filter into a device detecting the chemical complex, such as a microscope. The filter is employed by the tester to concentrate and collect organisms from a water sample. Once collected, the immobilized bacteria are exposed to the chemical complex and are detected in the manner described.

One other kit embodiment includes a nitrocellulose filter having antibodies immobilized on the filter. The antibodies may be an element of antisera, either monoclonal or polyclonal, applied to the nitrocellulose filter. The antibodies are directed to specific antigens of a particular type of bacteria. Examples of such antibodies are disclosed by Doyle (U.S. Pat. No. 5,168,063) and R. Szabo et al., *Appl. & Environ. Microbiol.*, 56, 3546 (1990).

Once captured and bound on the filter, the bacteria are visualized with the polymyxin B-containing chemical tag. The chemical tag may include biotin on a water soluble polymer backbone with the biotin highly iterated on the polymer. To detect the endotoxin, it is contemplated that one would also use such a filter to collect endotoxin and then tag the endotoxin with the chemical tag to make the complex described.

Specific examples of the method, chemical tag and complex of the present invention are presented in the Examples that follow. These examples are intended to describe particular aspects of the present invention and are not intended to limit the present invention.

EXAMPLES

Example 1
Preparation of a polymerizable Polymyxin B Derivative:

A quantity of 0.0065 g. of methacrylic acid obtained from Sartomar of Exton, Pa., was dissolved in a quantity of 1 µmole, in 5 mL, 0.004M phosphate buffer having a pH of 6.5 to form a methacrylic acid solution. Once dissolved, a quantity of 0.028 g of ethylaminodiethylaminopropyl carbodiimide (EDC) was added to the methacrylic acid solution. The EDC was obtained from Sigma Chemical of St. Louis, Mo. The quantity of EDC added was 2.0 equivalents. The resulting solution was stirred at room temperature for 1 hour to form an active ester.

A quantity of 0.1 g of polymyxin B pentasulfate obtained from Sigma of St. Louis, Mo., was added to a solution of 5 mL of 0.05M sodium bicarbonate to form a PMB solution. The PMB solution was added to the active ester to form a reaction mixture. The reaction mixture was incubated for about 4 hours at room temperature to form a PMB acrylamide product. The resulting product was purified by dialysis in a 500 MWCO dialysis membrane obtained from Spectrum Medical Labs of Los Angeles, Calif., to remove unreacted monomer and water soluble urea product from the product. The product conversion was at least 95% derivative as estimated by thin layer chromatography (TLC). The reaction is as follows:

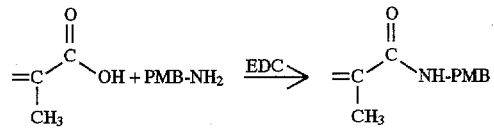

Example 2
Preparation of a Fluorescent Water Soluble Copolymer:

A terpolymer was prepared by dissolving a quantity of 0.030 g of the PMB acrylamide made in Example 1 into 10 g of water. Once dissolved, a quantity of 1.0 g of acrylamide obtained from Eastman Chemical of Signal Hill, Calif., and 0.010 g of N-fluoresceinylacrylamide was prepared according to a conventional procedure. One conventional procedure is described in an article of C. Munkholm and D. R. Walt et al., *Anal. Chem.*, v. 58, p. 1427 (1986).

A reaction was carried out in a gas-tight 125mL Ehrlenmeyer flask sealed with a rubber septum to permit replacement of atmosphere within the flask with an inert gas such as nitrogen. The reaction was initiated by addition of 0.005 g of VA 044, bis azo isobutyramidine (WAKO), a water soluble initiator yielding a cationic end group on the polymer. This type of initiator is favored over peroxide type initiators since it results in higher yields of a linear polymer with less branching. The reaction mixture was statically incubated for sixteen hours at 60° C. The copolymer was purified by both precipitation from acetone and dialysis in a 12,000 MWCO membrane.

A strain of *E. coli*, DH5α, was obtained from the University of Minnesota. The *E. coli* organisms were maintained on LB agar.

Individual colonies of microorganisms were selected and suspended in a phosphate buffered saline, (PBS) or other buffers conventionally used. One to two colonies of the *E. coli* microbes were suspended in PBS and treated with 0.05 mL of 10% solids w/w polymer solution. The microorganisms were then captured by filtration through a 0.22 µm Versapor™, manufactured by the Gelman Corp. of Ann Arbor, Mich., having a 13 mm diameter membrane.

The retained material was washed with several volumes of either 10 mL PBS or 0.05M phosphate buffer or 0.5M sodium chloride. The bacterial biomass was visualized with a hand held 366 nm U.V. lamp. Negative controls retained on the membrane exhibited no fluorescence. Control samples containing suspensions of *S. aureus* cells obtained from the ATCC also exhibited no fluorescence when stained and subsequently captured by the filter assay technique.

Example 3
Preparation of Polymyxin B Biotin Derivative:

To obtain a sensitivity higher than that shown in Example 3, an ELISA type approach was adopted. For comparison, a direct coupling of polymyxin B to horseradish peroxidase (HRP) was found unsatisfactory in a microbial filter capture assay because of an extremely high background binding of the polymyxin B—HRP conjugate to a commercial microporous membrane.

In the present invention, the polymyxin B was coupled to biotin, the microorganisms were treated in suspension, captured on a membrane filter and then labeled with avidin-horseradish peroxidase conjugate which could then be visualized in situ. The reaction to prepare polymyxin B biotin is as follows:

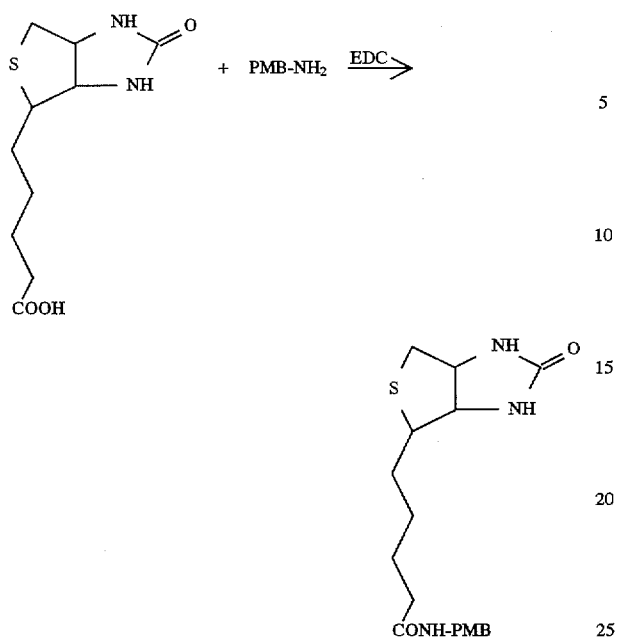
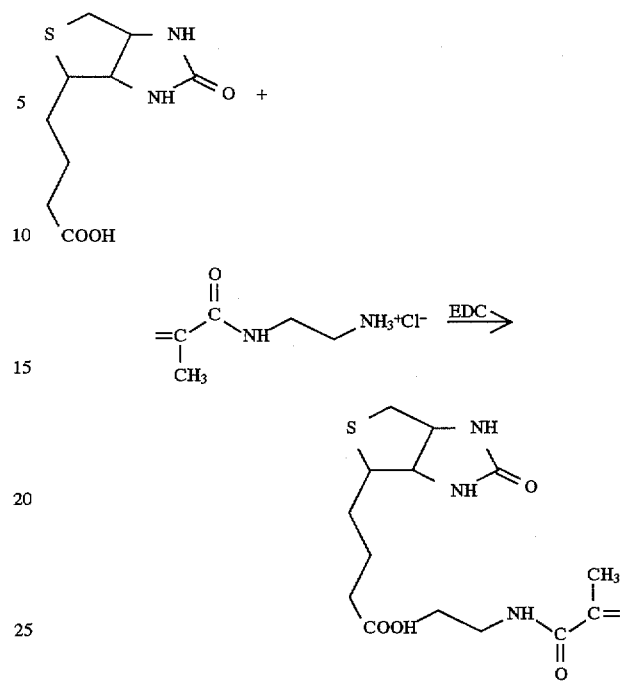

Biotin, obtained from Sigma chemical, was dissolved in a concentration of 0.0185 g, 1 µmole, in 5mL absolute ethanol and 10 mL of 0.02M phosphate buffer having a pH of 7.2. A quantity of 0.028 g of ethylaminodiethylaminopropyl carbodiimide, (EDC) was added in a concentration of 1.3 equivalents with stirring at room temperature for 30 minutes. A quantity of 0.1 g of polymyxin B in 10 mL of phosphate buffer having a pH of 7.2 was added with stirring for 6 hours at room temperature. The product was purified by dialysis against a phosphate buffer in a 500 MWCO membrane to remove unreacted materials.

Example 4
Evaluation of the Polymyxin B Biotin Probe on *E. Coli* and Gram Positive Strains:

A single colony of *E. coli* strain DH5α obtained from the University of Minnesota was selected from an agar plate and suspended in 2 mL of 0.02M phosphate, 0.15M sodium chloride at a pH of 7.2 to form a buffer. The bacterial suspension was treated with 0.05 mL, of 0.5 mg PMB-biotin probe as described in Example 4 at room temperature. The cells of the bacterial suspension were captured on a 13 mm microporous membrane disc by filtration, washed with 5 mL of the same buffer and treated in situ with 10 µg per mL of avidin-horseradish peroxidase obtained from Sigma Chemical in the same buffer containing 5 mg per mL of bovine serum albumin, also obtained from Sigma Chemical.

The membrane was washed with 5mL of the phosphate buffered saline. Cells were visualized by immersing the membrane in 5 mL of a diaminobenzidine/hydrogen peroxide reagent obtained as Fast Tabs™ from Sigma Chemical. Negative controls and gram positive cells such as *S. aureus* and *M. luteus* yielded virtually white discs. However, *E. coli* cells present in only a single quantity yielded a dark brown reaction on the test disc.

Example 5
Preparation of the Water Soluble Copolymer Components Biotinylmethacrylamide and Polymyxin B Methylacrylamide Biotinylmethacrylamide is prepared according to the following reaction scheme:

A quantity of 0.3 g d-Biotin obtained from Sigma Chemical was dissolved in 35 mL of absolute ethanol with 20 mL of phosphate buffer at a pH of 7.5 and activated by addition of 0.35 g of EDC at a concentration of 1.5 equivalents, along with 8 mL of pyridine which was added as a base catalyst. Activation proceeded at room temperature for 30 minutes. After all the reactants were solubilized, 0.22 g of N-aminopropyl-methacrylamide was added to the reaction mixture and stirred for several hours at room temperature. The ethanol solvent was stripped from the mixture by distillation and a residue was washed with several volumes of diluted acetic acid at a concentration of 0.1% v/v.

Polymyxin B methacrylamide was prepared according to a similar reaction protocol (Ex. 1). Specifically, 0.0065 g methacrylic acid was dissolved in 5 mL of 0.004M sodium phosphate buffer having a pH of 6.5. A quantity of 0.025 g of EDC was added with stirring for 40 minutes at room temperature. A quantity of 0.1 g of polymyxin B pentasulfate was added in 5 mL of a 0.05M phosphate buffer having a pH of 7.5 to form a reaction mixture. The reaction mixture was coupled for several hours and subsequently dialyzed in a 500 MWCO membrane against 2 L phosphate buffer.

Example 6
Preparation of Biotinylated, PMB Copolymer

A quantity of 0.3 g of biotinylmethacrylamide prepared in Example 6 was dissolved in 20 mL of ethanol:water in a 50:50 solution to form a biotinylmethacrylamide solution. This solution was added to the 0.1 g of PMB methacrylamide in 20 mL phosphate buffer. A quantity of 2.6 g of acrylamide was also dissolved. The entire sample was placed in a 125 mL Ehrlenmeyer flask and a quantity of 0.007 g VA 044 was added. The flask was sealed under nitrogen at atmospheric pressure and incubated at 55° C. for 12 hours to produce a copolymer. The copolymer obtained was purified by dialysis in a 2000 MWCO membrane against phosphate buffer. A representation of the linear copolymer is given the following scheme, wherein n is greater than m, and is determined from the mole ratio of monomers.

Biotinylmethacrylamide + PMB methacrylamide + VA O44 + acrylamide ⟶

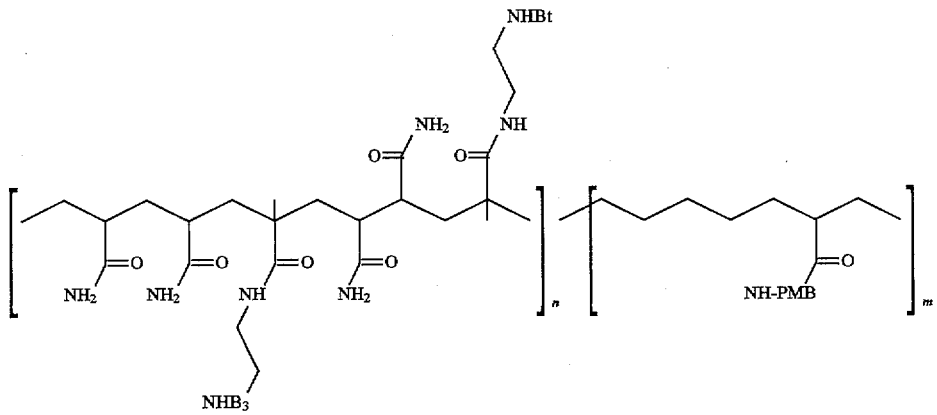

It is contemplated that the method and chemical tag of the present invention are suitable for use with binding agents other than polymyxin B to detect analytes other than LPS. For instance, it is believed that binding agents such as protein A, protein B and other immunogenic as well as non-immunogenic binding agents can be bonded to the chemical tag described. Other binding agents include an antibiotic that binds to an outer membrane of an analyte. In addition to the polymyxin antibiotic, it is believed that other antibiotics of the class of cationic oligopeptide antibiotics are suitable binding agents. Other members of this class include the colistins.

Example 7
Preparation of Biotinyated Polymer

A quantity of 0.3 g of the biotinylmethacrylamide prepared as described in example 6 was dissolved in 15 mL ethanol water (50:50) and added to 2.0 g of acrylamide in 20 mL water. Polymerization initiator, VA 044, 0.010 g was dissolved in the reaction mixture. The sample was sealed in a 125 mL Ehrienmeyer flask with a tightly fitting rubber septum. The atmosphere was flushed and replaced with nitrogen and incubated statically for 18 hours at 55° C. The resultant polymer was purified by dialysis against 0.2M sodium phosphate buffer.

Example 8
Evaluation of the Signal Amplification Polymer

One small colony of *E. coli* DH5α was suspended in a solution of phosphate buffered saline to make a suspension. The suspension was diluted 5,000 and the suspension was then treated with 0.5 mg of PMB-biotin conjugate in accordance with a protocol described in Example 5. Cells captured by the PMB-biotin conjugate were treated in situ with a solution of 2 µg per mL of Streptavidin obtained from Bethesda Research Laboratories of Bethesda, Md. in a phosphate buffered saline solution with 5 mg per mL bovine serum albumin. The cells, now immobilized, were washed with a phosphate buffered saline that also included a surfactant. The cells were then treated with 5 mL of the polymer of Ex. 8 in phosphate buffered saline having a concentration of 10% solids, by weight and subsequently treated with 10% solids, by weight and subsequently treated with 10 µg per mL of avidin horseradish peroxidase conjugate in a phosphate buffered saline (PBS) bovine serum albumin (BSA) solution. The cells were then washed and visualized with diaminobenzidine-hydrogen peroxide tablets.

The samples diluted 5,000 and 150,000 fold were readily visualized over negative controls. Independent plating experiments established that one colony contains approximately 10,000,000 colony forming units (CFU) by standard plating dilution methods. From this data, it is estimated that the highest dilution enabling an easy visualization is 80 CFU on a membrane.

Based on the density of LPS molecules per cell and molecular weight, 1,000,000 molecules and 1,700 molecules respectively, it is estimated this quantity of cells to be 0.86 picograms of LPS on the 11 mm membrane. It is believed that higher sensitivity can readily be achieved by any number of adjustable parameters. Conceivably, one to ten bacterial cells could be visualized using this method.

All publications and patents cited hereinabove are incorporated by reference herein, as though fully set forth. Although the present invention has been described with reference to preferred embodiments, workers skilled in the art will recognize that changes may be made in form and detail without departing from the spirit and scope of the invention.

What is claimed is:

1. A detectable synthetic copolymer comprising repeating monomeric units, wherein a first population of the monomeric units each comprises a binding agent which binds to a microorganism having multiple binding sites for said binding agent and wherein a second population of the monomeric units each comprises a detectable label or a binding site for a detectable label.

2. The synthetic copolymer of claim 1 wherein the copolymer includes more of said second monomeric units than of said first monomeric units.

3. The synthetic copolymer of claim 1 wherein the microorganism is a pathogenic bacterium.

4. The synthetic copolymer of claim 1 wherein the detectable label or the binding site for the detectable label is bound to each of the population of said second monomeric units via a linking moiety.

5. The synthetic copolymer of claim 2 wherein the detectable label is a fluorescent molecule.

6. The synthetic copolymer of claim 2 wherein the copolymer includes a ten-fold excess of second monomeric units.

7. The synthetic copolymer of claim 5 which comprises a water-insoluble polymeric microsphere.

8. The synthetic copolymer of claim 1 wherein the binding site for the detectable label is biotin.

9. The synthetic copolymer of claim 1 wherein the binding agent is an antibiotic or a fragment thereof.

10. The synthetic copolymer of claim 9 wherein the antibiotic is polymyxin B or the nonapeptide fragment thereof.

11. A method for detecting the presence of microorganisms in a test sample comprising:

(a) immobilizing microorganisms from said test sample;

(b) contacting said microorganisms with an amount of a detectable synthetic copolymer which comprises repeating monomeric units, wherein a first population of the monomeric units each comprises a binding agent which binds to said microorganisms at multiple binding site for said binding agent on each microorganism, and wherein a second population of the monomeric units each comprises a detectable label or a binding site for a detectable label, so as to form microorganism-copolymer complexes; and (c) detecting said microorganism-copolymer complexes.

12. The method of claim 11 wherein the second population of monomeric units is larger than the first population of monomeric units.

13. The method of claim 11 wherein the detectable synthetic copolymer is essentially linear.

14. The method of claim 11 wherein the binding agent is an antibiotic or a fragment thereof, which binds to binding sites on a pathogenic microorganism.

15. The method of claim 14 wherein the microorganism is a bacterium.

16. The method of claim 15 wherein the microorganism is *E. coli*.

17. The method of claim 14 wherein the detectable label is a fluorogenic molecule.

18. The method of claim 14 wherein the binding site for the detectable label is a biotin molecule.

19. The method of claim 18 wherein the complexes are detected by reaction of the biotin with enzyme labelled avidin followed by a substrate for the enzyme that yields a detectable reaction product.

20. The synthetic copolymer of claim 1 which is essentially linear.

21. The method of claim 14 wherein the antibiotic is polymyxin B or the nonapeptide fragment thereof.

22. A detectable synthetic copolymer comprising repeating monomeric units prepared by copolymerizing a first population of monomeric units, each comprising a binding agent which binds to a microorganism having multiple binding sites for said binding agent, and a second population of monomeric units, each comprising a detectable label or a binding site for a detectable label.

23. The synthetic copolymer of claim 22 wherein the copolymer includes a greater number of said second monomeric units than of said first monomeric units.

24. The synthetic copolymer of claim 23 wherein the copolymer includes a ten-fold excess of second monomeric units.

25. The synthetic copolymer of claim 22 which is essentially linear.

26. The synthetic copolymer of claim 22 wherein the microorganism is a pathogenic bacterium.

27. The synthetic copolymer of claim 22 wherein the detectable label or the binding site for the detectable label is bound to each of the population of said second monomeric units via a linking moiety.

28. The synthetic copolymer of claim 23 wherein the detectable label is a fluorescent molecule.

29. The synthetic copolymer of claim 28 which comprises a water-insoluble polymeric microsphere.

30. The synthetic copolymer of claim 22 wherein the binding site for the detectable label is biotin.

31. The synthetic copolymer of claim 22 wherein the binding agent is an antibiotic or a fragment thereof.

32. The synthetic copolymer of claim 31 wherein the antibiotic is polymyxin B or the nonapeptide fragment thereof.

* * * * *